(12) United States Patent
Carlucci et al.

(10) Patent No.: US 8,993,830 B2
(45) Date of Patent: Mar. 31, 2015

(54) ABSORBENT ARTICLES COMPRISING AN IRON COMPLEXING AGENT

(75) Inventors: Giovanni Carlucci, Chieti (IT); Antonella Pesce, Rome (IT)

(73) Assignee: The Procter & Gamble Company, Cincinnati, OH (US)

( * ) Notice: Subject to any disclaimer, the term of this patent is extended or adjusted under 35 U.S.C. 154(b) by 534 days.

(21) Appl. No.: 12/828,490

(22) Filed: Jul. 1, 2010

(65) Prior Publication Data

US 2011/0004174 A1 Jan. 6, 2011

(30) Foreign Application Priority Data

Mar. 7, 2009 (EP) .................................... 09008733

(51) Int. Cl.
| | | |
|---|---|---|
| *A61F 13/20* | (2006.01) | |
| *A61F 13/42* | (2006.01) | |
| *A61L 15/56* | (2006.01) | |
| *A61L 15/20* | (2006.01) | |

(52) U.S. Cl.
CPC ...... *A61L 15/56* (2013.01); *A61L 15/20* (2013.01)
USPC ....................................... 604/361

(58) Field of Classification Search
CPC .................................................. A61F 13/202

USPC ............ 604/317, 361, 404, 904; 28/118–120; 424/430–449
See application file for complete search history.

(56) References Cited

U.S. PATENT DOCUMENTS

| | | | | |
|---|---|---|---|---|
| 5,217,444 | A | * | 6/1993 | Schoenfeld ................... 604/361 |
| 6,951,911 | B2 | | 10/2005 | Tagawa et al. |
| 7,087,669 | B2 | | 8/2006 | Ota et al. |

FOREIGN PATENT DOCUMENTS

| | | |
|---|---|---|
| EP | 0 257 951 A2 | 3/1988 |
| WO | WO 01/79314 A1 | 10/2001 |
| WO | WO 02/05949 A1 | 1/2002 |
| WO | WO 2005/039656 A1 | 5/2005 |

OTHER PUBLICATIONS

PCT International Search Report, mailed Nov. 26, 2009, 6 pages.
Database Embase, Elsevier Science Publishers, Amsterdam, NL; 1955, Matubara T: "A new method for the determination of serum iron" XP002557453.

* cited by examiner

*Primary Examiner* — Tan-Uyen T Ho
*Assistant Examiner* — Peter S Vasat
(74) *Attorney, Agent, or Firm* — Andres E. Velarde; Brian M. Bolam

(57) ABSTRACT

An absorbent article for menses absorption comprising an iron complexing agent, which is able to change the menses color.

5 Claims, No Drawings

ABSORBENT ARTICLES COMPRISING AN IRON COMPLEXING AGENT

FIELD OF THE INVENTION

The present disclosure is directed to absorbent articles for feminine hygiene and in particular to articles for menses absorption which include an iron complexing agent.

BACKGROUND OF THE INVENTION

Absorbent articles for feminine hygiene are known in the art. Typical examples include sanitary napkins, pantyliners, vaginal tampons or interlabial pads. Such articles are often used to absorb and retain bodily fluids and other exudates excreted by the human body.

Fluids are often retained in absorbent articles within an absorbent element comprising absorbent materials which often include superabsorbent materials, such as absorbent gelling materials (AGM), usually in finely dispersed form, e.g. typically in particulate form. Conventional superabsorbent materials known in the art for use in absorbent articles typically comprise water insoluble, water swellable, hydrogel forming crosslinked absorbent polymers which are capable of absorbing large quantities of liquids and of retaining such absorbed liquids under moderate pressure. In general, absorbent articles for feminine hygiene comprising conventional absorbent gelling materials commonly have good absorption and retention characteristics to bodily fluids such as menses. However there is still a need to provide an absorbent article for feminine hygiene which keeps a pleasant visual appearance during and after its usage. Furthermore, it would be desirable to make the user aware of the fact that the article is saturated and needs consequently to be replaced.

The inventors have now found a way to solve these problems, by providing an absorbent article for feminine hygiene comprising an iron complexing agent which changes the menses color when it comes into contact with them.

SUMMARY OF THE INVENTION

The present invention relates to an absorbent article for feminine hygiene comprising an iron complexing agent selected from the group consisting of 2,2'-dipyridylamine, o-phenanthroline, di-2-pyridyl ketone, 2-furildioxime and any combinations thereof.

DETAILED DESCRIPTION OF THE INVENTION

The term "absorbent article for feminine hygiene" is used herein in a very broad sense including any article able to receive and/or absorb and/or contain and/or retain fluids and/or exudates, especially body fluids/bodily exudates such as menses. Exemplary absorbent articles for feminine hygiene in the context of the present invention are disposable absorbent articles for feminine hygiene. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles for feminine hygiene according to the present invention are sanitary napkins, panty liners, tampons, interlabial devices or the like. Absorbent articles suitable for use in the present invention include any type of structures, from a single absorbent layer to more complex multi layer structures. Certain absorbent articles include a fluid pervious topsheet, a backsheet, which may be fluid impervious and/or may be water vapour and/or gas pervious, and an absorbent element often called "core" comprised there between.

The term "use" or "usage", as used herein with reference to absorbent articles, refers to the period of time that starts when the absorbent article is actually put in contact with the anatomy of a wearer.

By "body fluid" it is meant herein any fluid produced by human body including, but not limited to, perspiration, urine, menstrual fluids, vaginal secretions and the like.

The term "layer", as used herein with reference to absorbent articles, refers to any element which may be comprised within the absorbent article including, but not limited to, topsheet, backsheet and absorbent element.

The term "saturated", as used herein, means that the article is not capable anymore of absorbing and retaining body fluids such as menses without risk of leakages.

The term "attached", as used herein, encompasses configurations whereby a first element is directly secured to another element by affixing the first element directly to a second element and whereby a first element is indirectly secured to a second element by affixing the first element to a third, intermediate member(s), which in turn are affixed to the second element.

The present invention relates to an absorbent article for feminine hygiene comprising an iron complexing agent selected from the group consisting of 2,2'-dipyridylamine, o-phenanthroline, di-2-pyridyl ketone, 2-furildioxime and any combinations thereof.

When the iron complexing agent comes in contact with menses, it changes their color from dark red to orange. Without being bound by theory, it is believed this is due to the capacity of the iron complexing agent to form strong complexes with iron ions which are extracted from hemoglobin.

This color change might not only render the fully or partially used article more pleasant to look at but also somehow mask the strong color of the menses by turning it into a lighter colour, and can also be used as an indicator of how much the absorbent article (or an area of it) is loaded with menses.

In some embodiments, the absorbent article may comprise an absorbent element intended to retain body fluids such as menses which may include natural or synthetic absorbent fibers or foams and/or one or more superabsorbent polymers. In some embodiments, the iron complexing agent may be comprised within the absorbent element. In these cases, the iron complexing agent may be incorporated in any manner available to the skilled man such as finely dispersed within the absorbent element and/or partially or totally absorbed within the absorbent fibers or the superabsorbent polymers of the absorbent element, or coated or printed on or within the absorbent element.

In some embodiments, the absorbent article may comprise a fluid pervious topsheet, a backsheet and an absorbent element, said absorbent element being positioned between said topsheet and said backsheet. In these embodiments, the iron complexing agent may be comprised within or applied over the topsheet, the backsheet and/or the absorbent element, and/or may be comprised within or applied over additional elements interposed between them in any way which allow the contact of the iron complexing agent with menses upon use of the article and which allow menses color change to be noticed by the user eyes.

In some embodiments, the iron complexing agent may be uniformly distributed over the whole surface of the article or over the whole surface of the layer on which it is applied or may be uniformly distributed within the whole layer of the article in which it is included.

In other embodiments, the iron complexing agent may be distributed only over a portion of the surface of the article or only over a portion of the surface of the layer on which it is applied or may be distributed only within a portion of the layer in which it is included. In these cases the iron complexing agent may be applied as one or more patches, strips or combination thereof.

In some embodiments, the iron complexing agent may be located on an indicating device selected from the group consisting of patches and strips and combination thereof which is attached to the topsheet or inserted into the article. The indicating device may be inserted into the article between the topsheet and the absorbent element of the absorbent article.

Given that the reaction between hemoglobin and the iron complexing agent is roughly stoichiometric, the iron complexing agent may be used to indicate to the wearer that the article is saturated and needs consequently to be replaced. Hence, when the article is saturated, menses color change does not occur any more when the iron complexing agent comes in contact with them and the area of the article wherein the iron complexing agent is present loses its orange color and turns to red.

In some embodiments, the amount of the iron complexing agent present in the absorbent article may be from 0.1 to 2500 mg per each absorbent article, or from 1 to 1000 mg per each absorbent article, or from 5 to 500 mg per each absorbent article, or from 10 to 250 mg per each absorbent article.

In some embodiments, the absorbent article for feminine hygiene may be a sanitary napkin, an interlabial pad, a vaginal tampon or a pantyliner.

In some embodiments, the iron complexing agent may be distributed within or over the absorbent article or may be applied on an indicating device in any form, including in dry powder form, as a suspension in a liquid or as a solution. Suitable solvents for use herein are, for example, alcohols or acetone. In the cases where the iron complexing agent is distributed within or over the absorbent article or applied on an indicating device as a suspension in a liquid or as a solution, the absorbent article or the indicating device needs to be dried so that a dried residue remains within or over the article or on the indicating device. In the embodiments where the iron complexing agent is located on an indicating device which is attached to the topsheet or inserted into the article, the iron complexing agent may be applied in a pattern such as a plurality of zones, dots or text that change color when the iron complexing agent changes color.

An absorbent article according to the present invention has a more pleasant visual appearance during the time of use since the iron complexing agent changes the color of menses when it comes in contact with them.

EXAMPLE

A feminine pad Always™ Regular as sold by The Procter & Gamble Company is opened by cutting the wrap around the perforated coverstock at its bottom face approximately along a longitudinal edge of the release paper, which covers the external adhesive layer. The side of the absorbent fibrous core is then exposed by slightly shifting the water impermeable plastic bottom layer and subsequently, the fibrous core is split into two halves, each having approximately the same thickness, along a plane, which is parallel to the plane of the napkin itself. 200 mg of o-phenanthroline powder are homogeneously distributed between these two fibrous layers, which are then joined together to reconstitute the absorbent core. The water impermeable inner backsheet is then put back into its original position and the wrap around perforated coverstock is sealed along the cut by means of e.g. a double-sided adhesive tape.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for feminine hygiene comprising an iron complexing agent selected from the group consisting of 2,2'-dipyridylamine, di-2-pyridyl ketone, o-phenanthroline, 2-furildioxime and any combinations thereof; wherein the absorbent article is a vaginal tampon; and wherein the iron complexing agent is capable of interacting with menses absorbed by the absorbent article to change the appearance of the menses.

2. An absorbent article for feminine hygiene according to claim 1, wherein the iron complexing agent is comprised within the absorbent element.

3. An absorbent article for feminine hygiene according to claim 1, wherein the iron complexing agent is located on an indicating device.

4. An absorbent article for feminine hygiene according to claim 3, wherein the indicating device is selected from the group consisting of patches and strips and combination thereof and is attached to the topsheet or inserted into the article.

5. An absorbent article for feminine hygiene according to claim 1 comprising the iron complexing agent at a total level of from 0.1 to 2500 mg per each absorbent article.

* * * * *